US012606586B2

(12) United States Patent
Xu et al.

(10) Patent No.: US 12,606,586 B2
(45) Date of Patent: Apr. 21, 2026

(54) METHOD FOR PURIFYING SUCRALOSE-6-ACETATE

(71) Applicant: ANHUI JINHE INDUSTRIAL CO., LTD., Chuzhou (CN)

(72) Inventors: Chuanjiu Xu, Chuzhou (CN); Chenggang Xu, Chuzhou (CN); Yongle Chen, Chuzhou (CN)

(73) Assignee: Anhui Jinhe Industrial Co., Ltd., Chuzhou (CN)

( * ) Notice: Subject to any disclaimer, the term of this patent is extended or adjusted under 35 U.S.C. 154(b) by 407 days.

(21) Appl. No.: 18/250,957

(22) PCT Filed: Nov. 27, 2020

(86) PCT No.: PCT/CN2020/132262
§ 371 (c)(1),
(2) Date: Apr. 27, 2023

(87) PCT Pub. No.: WO2022/110017
PCT Pub. Date: Jun. 2, 2022

(65) Prior Publication Data
US 2024/0327445 A1 Oct. 3, 2024

(51) Int. Cl.
*C07H 13/04* (2006.01)
*C07H 1/06* (2006.01)

(52) U.S. Cl.
CPC .............. *C07H 13/04* (2013.01); *C07H 1/06* (2013.01)

(58) Field of Classification Search
CPC ................................... C07H 13/04; C07H 1/06
See application file for complete search history.

(56) References Cited

U.S. PATENT DOCUMENTS 5,530,106 A * 6/1996 Navia ..................... C07H 13/08
536/127
2003/0171575 A1* 9/2003 Catani ...................... C07H 5/02
536/119
2010/0022765 A1* 1/2010 Ho .......................... C07H 13/04
536/123.13

FOREIGN PATENT DOCUMENTS

CN 101328195 A 12/2008
CN 101709069 A 5/2010
CN 108250255 A 7/2018
CN 109734755 A 5/2019
CN 109956983 A 7/2019
CN 111000803 A 4/2020

OTHER PUBLICATIONS

CN1271077C, 2006, machine translation. (Year: 2006).*
Giulietti, Crystallization by Antisolvent Addition and Cooling, Sep. 2012, Crystallization—Science and Technology, Chapter: Crystallization by Antisolvent Addition and Cooling, Publisher InTech. (Year: 2012).*
Office Action for CN 202080003566.3 issue Aug. 16, 2022.
Office Action for CN 202080003566.3 issue Dec. 29, 2021.
International Search Report for PCT/CN2020/132262 dated Sep. 2, 2021.

* cited by examiner

*Primary Examiner* — Layla D Berry
(74) *Attorney, Agent, or Firm* — Knobbe, Martens Olson & Bear LLP

(57) ABSTRACT

Provided is a method for purifying sucralose-6-acetate, including: preparation: providing a saturated solution of crude sucralose-6-acetate in ethyl acetate that is heated to a predetermined temperature; gradient crystallization: subjecting the saturated solution to multiple cooling crystallization and filtration, and collecting crude sucralose-6-acetate obtained after the multiple cooling crystallization and filtration, where during each cooling crystallization process, a low-polarity solvent is added dropwise to the saturated solution to reduce a polarity of the saturated solution during crystallization step by step; and purification: subjecting a collected crude sucralose-6-acetate to recrystallization for purification by using a mixed solution of ethyl acetate and the low-polarity solvent to obtain fine sucralose-6-acetate of high purity.

8 Claims, 3 Drawing Sheets

METHOD FOR PURIFYING SUCRALOSE-6-ACETATE

CROSS REFERENCE TO RELATED APPLICATION

This application is a U.S. National Phase Application of PCT International Application Number PCT/CN2020/132262, filed on Nov. 27, 2020, designating the United States of America and published in the Chinese language. The disclosures of the above-referenced application are hereby expressly incorporated by reference in its entirety.

TECHNICAL FIELD

The present disclosure relates to the technical field of chemical purification, and in particular to a method for purifying sucralose-6-acetate.

BACKGROUND

Sucralose-6-acetate is one of the important intermediates for producing sucralose, and the purity of sucralose-6-acetate is one of the keys affecting the yield of sucralose. It is found that, when the purity of sucralose-6-acetate is 80%, the yield of sucralose after deacylation is 45%; but when the purity of sucralose-6-acetate is increased to 90%, the yield of sucralose is accordingly increased to 67%. Therefore, the improvement of the purity of sucralose-6-acetate makes it possible to effectively improve the yield of sucralose. At present, ethyl acetate, butyl acetate and water are widely used industrially for the purification of sucralose-6-acetate, and the purification of sucralose-6-acetate is generally achieved by multiple recrystallization.

There are patent reports on the purification of sucralose-6-acetate. Chinese patent CN101328195 discloses a method for purifying sucralose-6-acetate by recrystallization with ethyl acetate and water, which is a previous sucralose-6-acetate purification technology used in industry, and has the advantages of high single-pass yield, but the disadvantages of low product purity, multiple recrystallization, and large solvent consumption.

Chinese patent CN101709069 discloses a method for purifying sucralose-6-acetate, including: first preparing a sucralose-6-acetate crude product into an aqueous solution, and then subjecting the aqueous solution to extraction with ethyl acetate or butyl acetate, concentration, and multiple recrystallization by the above solvent, to obtain a sucralose-6-acetate crystal. However, the above method has the disadvantages of large organic solvent consumption, low product purity, and poor purification and separation effect.

Industrially, sucralose-6-acetate is obtained through chlorination of sucrose-6-acetate, and by-products produced during the chlorination mainly include monochlorosucrose-6-acetate, dichlorosucrose-6-acetate, tetrachlorosucrose-6-acetate, or the like, where monochlorinated and dichlorinated by-products are common. Ethyl acetate, which is commonly used in industry, has excellent polarity and includes an ester group. According to the principle of similar compatibility, ethyl acetate has a high solubility for the four products. However, the use of a single solvent inevitably fails to effectively separate a variety of by-products; thus, it is easy to cause problems in the current process such as poor crystallization efficiency of ethyl acetate, large number of crystallization times, and large organic solvent consumption.

SUMMARY

In view of the above problems, the present disclosure provides a method for purifying sucralose-6-acetate in order to overcome the above problems.

To achieve the above object, the present disclosure provides the following technical solutions:

A method for purifying sucralose-6-acetate, including:

preparation: providing a saturated solution of crude sucralose-6-acetate in ethyl acetate which is heated to a predetermined temperature;

gradient crystallization: subjecting the saturated solution to multiple cooling crystallization and filtration, and collecting crude sucralose-6-acetate obtained after the multiple cooling crystallization and filtration, where during each cooling crystallization process, a low-polarity solvent is added dropwise to the saturated solution to reduce a polarity of the saturated solution during crystallization step by step; and purification: subjecting the collected crude sucralose-6-acetate to a recrystallization for purification by using a mixed solution of ethyl acetate and the low-polarity solvent to obtain fine sucralose-6-acetate of high purity.

In some embodiments, the predetermined temperature of the saturated solution of crude sucralose-6-acetate in ethyl acetate is in a range of 60° C. to 70° C.

In some embodiments, the low-polarity solvent is one or more selected from the group consisting of n-pentane, cyclopentane, n-hexane, cyclohexane, n-heptane, and cyclo-heptane.

In some embodiments, in the gradient crystallization, the saturated solution is subjected to the cooling crystallization for three or more times.

In some embodiments, in the gradient crystallization, the saturated solution is subjected to the cooling crystallization for three times, where a first cooling crystallization is conducted at a temperature of 40° C. to 50° C., a second cooling crystallization is conducted at a temperature of 20° C. to 30° C., and a third cooling crystallization is conducted at a temperature of –10° C. to 0° C.

In some embodiments, in the gradient crystallization, the low-polarity solvent is added dropwise for 5 minutes to 30 minutes in an amount of 5% to 15% of a volume of the saturated solution during each cooling crystallization process;

the first cooling crystallization is conducted for 0.5 hours to 1 hour, the second cooling crystallization is conducted for 0.5 hours to 1.5 hours, and the third cooling crystallization is conducted for 0.5 hours to 2 hours; and during each cooling crystallization process, a resulting solution is stirred at a rate of 10 r/min to 30 r/min.

In some embodiments, in the purification, the crude sucralose-6-acetate is dissolved at a temperature of 50° C. to 70° C. for recrystallization; the mixed solution of ethyl acetate and the low-polarity solvent is stirred at a rate of 60 r/min to 100 r/min; a volume ratio of ethyl acetate to the low-polarity solvent is in a range of 1:(0.5-1); and the recrystallization is conducted at a temperature of –10° C. to 0° C. for 0.5 hours to 3 hours.

In some embodiments, the purification further includes: drying a sucralose-6-acetate solid obtained by filtration with a dryer to obtain the fine sucralose-6-acetate of high purity.

In some embodiments, the method further includes:

recovery: collecting a first mother liquor obtained by filtration after the third cooling crystallization in the gradient crystallization and a second mother liquor obtained by filtration after the recrystallization for purification, and recovering ethyl acetate and the low-polarity solvent from the first mother liquor and the second mother liquor.

In some embodiments, in the recovery, under the condition that the low-polarity solvent includes one selected from the group consisting of n-pentane, cyclopentane, and n-hexane, the low-polarity solvent is first recovered from the first mother liquor and the second mother liquor, and then ethyl acetate is recovered; and under the condition that the low-polarity solvent includes one selected from the group consisting of cyclohexane, n-heptane, and cycloheptane, ethyl acetate is first recovered from the first mother liquor and the second mother liquor, and then the low-polarity solvent is recovered.

In summary, the present disclosure has the following beneficial effects:

In the method of the present disclosure, ethyl acetate is used as an initial solvent for cooling crystallization of sucralose-6-acetate, and a low-polarity solvent is added step by step with the decrease of temperature to make the polarity of the mixed solvent show a trend of gradient reduction during the crystallization, such that impurities could be effectively separated due to polarity changes, which enables high single-pass crystallization yield and efficiency of sucralose-6-acetate, ensures the purity of a crystallization product, and reduces the number of crystallization times and the consumption of the organic solvent, thereby leading to high product yield, purity, and quality.

DETAILED DESCRIPTION OF THE EMBODIMENTS

To make the object, technical solutions, and advantages of the present disclosure clear, embodiments of the present disclosure will be further described in detail with reference to the accompanying drawings. Although exemplary embodiments of the present disclosure are shown in the accompanying drawings, it should be understood that the present disclosure may be implemented in various forms and should not be limited to the embodiments set forth herein. Instead, these embodiments are provided to make the present disclosure thoroughly understood and make a protection scope of the present disclosure clear to those skilled in the art.

The by-products produced during the preparation of sucralose-6-acetate are mostly monochlorinated and dichlorinated by-products. Moreover, each chlorinated product has a specified polarity, and the polarity gradually increases with the increase of the number of chlorine groups, that is, the four products rank as follows in terms of polarity: tetrachlorosucrose-6-acetate>sucralose-6-acetate>dichlorosucrose-6-acetate>monochlorosucrose-6-acetate. Although ethyl acetate used in industry has excellent polarity and exhibits high solubility for the four chlorinated products, the recrystallization for purification using a single solvent inevitably fails to effectively separate a variety of by-products.

The technical concept of the present disclosure is as follows: An ethyl acetate saturated solution is used for cooling crystallization of sucralose-6-acetate, and a low-polarity solvent is added step by step with the decrease in temperature to reduce the polarity of the solution in stages, such that impurities could be effectively separated and a crystalline purity of sucralose-6-acetate could be improved at each stage, thereby reducing the number of crystallization times and the organic solvent consumption, and making it possible to ensure a high single-pass crystallization yield and the purity of a crystallization product. The method of the present disclosure has strong operability and makes it possible to obtain product with high yield, high purity, and good quality.

Figure 1:
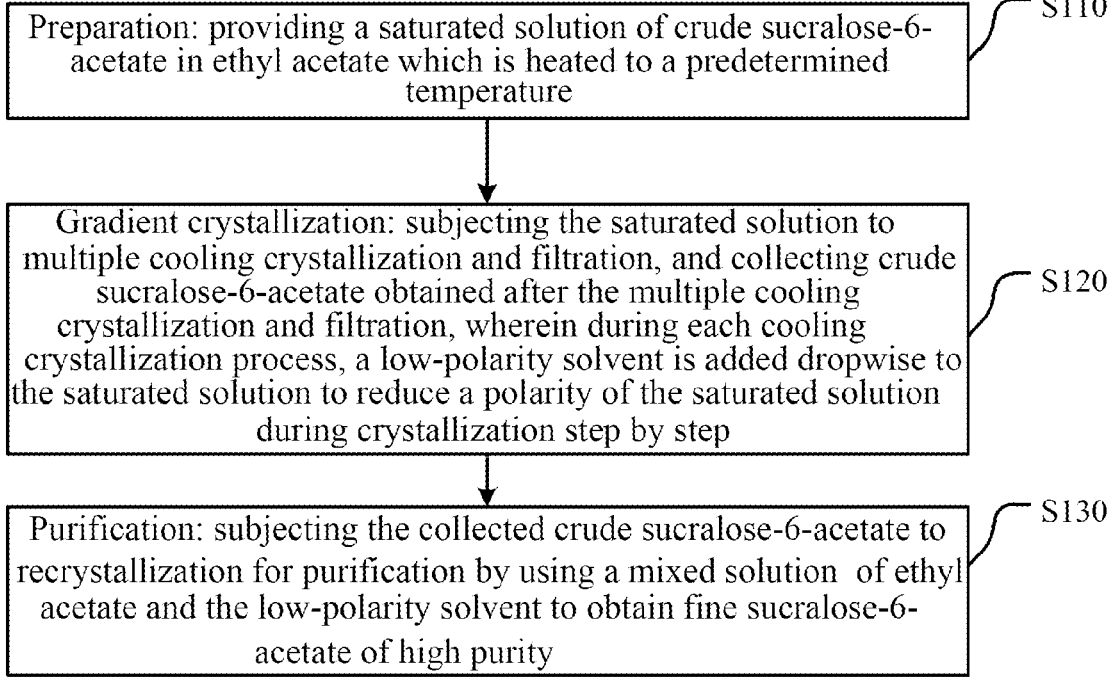
FIG. 1 is a flowchart showing the method for purifying sucralose-6-acetate according to an embodiment of the present disclosure.

FIG. 1 is a flowchart showing a method for purifying sucralose-6-acetate according to an embodiment of the present disclosure. As shown in FIG. 1, the method includes:

S110: Preparation: A saturated solution of crude sucralose-6-acetate in ethyl acetate that is heated to a predetermined temperature is provided.

The saturated solution of crude sucralose-6-acetate in ethyl acetate could be provided by a specified procedure in industry directly, or could be provided by dissolving/extracting crude sucralose-6-acetate with ethyl acetate.

S120: Gradient crystallization: The saturated solution of crude sucralose-6-acetate in ethyl acetate is subjected to multiple cooling crystallization and filtration, and crude sucralose-6-acetate obtained after the multiple crystallization and filtration is collected, where during each cooling crystallization process, a low-polarity solvent is added dropwise to the saturated solution to reduce a polarity of the saturated solution during crystallization step by step.

During the purification of sucralose-6-acetate, the temperature of the resulting solution gradually decreases with the progress of crystallization, and the contents of monochlorosucrose-6-acetate and dichlorosucrose-6-acetate increase relatively. Since the low-polarity solvent is added during each crystallization process in the present disclosure, the overall polarity of the solvent shows a trend of gradient reduction with the decrease in temperature, such that there are fewer and fewer high-polarity products are dissolved in the solution, which means that the trichlorinated product is precipitated in a large quantity and the monochlorinated product and the dichlorinated product with low polarity are rarely precipitated during the crystallization. Therefore, in the present disclosure, by adding the low-polarity solvent to the solution step by step, the polarity of the solution system is reduced in stages while the temperature decreases, thereby improving the single-pass yield and efficiency of sucralose-6-acetate at each stage of cooling crystallization, reducing the number of crystallization times, and reducing the organic solvent consumption.

S130: Purification: The crude sucralose-6-acetate obtained after the multiple cooling crystallization is subjected to recrystallization for purification by dissolving the crude sucralose-6-acetate in a mixed solution of ethyl acetate and the low-polarity solvent to obtain a fine sucralose-6-acetate of high purity.

Since the purity of the crude sucralose-6-acetate is improved at each stage of the gradient crystallization, under the condition of the same number of crystallization times, the purity of the final sucralose-6-acetate product in the embodiment is significantly improved.

In an embodiment of the present disclosure, the temperature of the saturated solution of crude sucralose-6-acetate in ethyl acetate is in a range of 60° C. to 70° C. Ethyl acetate has excellent polarity and includes ester groups. According to the principle of similar compatibility, ethyl acetate exhibits high solubility for the four chlorinated products, which could effectively ensure the product yield. In the present disclosure, ethyl acetate with excellent polarity is first used alone, and with the progress of cooling crystallization, a low-polarity solvent is gradually added to reduce the overall polarity of the solvent in the solution system, such that monochlorinated product and dichlorinated product of low polarity are effectively separated due to the gradient changes of the polarity of the solvent, which promotes the precipitation of the target product sucralose-6-acetate and realizes the efficient and high-purity purification of sucralose-6-acetate.

In an embodiment of the present disclosure, the low-polarity solvent is one or more selected from the group consisting of n-pentane, cyclopentane, n-hexane, cyclohexane, n-heptane, and cycloheptane. Of course, the low-polarity solvent available in the present disclosure is not limited to the above solvents, and any low-polarity solvent that can be mixed with ethyl acetate to produce a mixed solvent with reduced polarity, does not react with the target product in the solution, and is easy to separate may be used in the present disclosure.

In an embodiment of the present disclosure, in the gradient crystallization, the saturated solution is subjected to the cooling crystallization for three or more times.

In some preferred embodiments of the present disclosure, an excellent purification effect could be achieved by gradually reducing the polarity of the solvent and conducting cooling crystallization for 3 times. Of course, increased cooling crystallization times could bring an improved purification effect, but would also increase the cost. Therefore, the actual number of cooling crystallization times could be determined according to the production needs.

In an embodiment of the present disclosure, in the gradient crystallization, the saturated solution of crude sucralose-6-acetate in ethyl acetate is subjected to the cooling crystallization for three times, where a first cooling crystallization is conducted at a temperature of 40° C. to 50° C., a second cooling crystallization is conducted at a temperature of 20° C. to 30° C., and a third cooling crystallization is conducted at a temperature of −10° C. to 0° C.

In some embodiments, in the gradient crystallization, the low-polarity solvent is added dropwise for 5 minutes to 30 minutes in an amount of 5% to 15% of a volume of the saturated solution during each cooling crystallization process.

In some embodiments, the cooling crystallization is conducted for three times, where a first cooling crystallization is conducted for 0.5 hours to 1 hour, a second cooling crystallization is conducted for 0.5 hours to 1.5 hours, and a third cooling crystallization is conducted for 0.5 hours to 2 hours; and the resulting solution is stirred at a rate of 10 r/min to 30 r/min during each cooling crystallization process.

In an embodiment of the present disclosure, in the purification, the crude sucralose-6-acetate is dissolved at a temperature of 50° C. to 70° C. for recrystallization; the mixed solution of ethyl acetate and the low-polarity solvent is stirred at a rate of 60 r/min to 100 r/min; a volume ratio of ethyl acetate to the low-polarity solvent is in a range of 1:(0.5-1); and the recrystallization is conducted at a temperature of −10° C. to 0° C. for 0.5 hours to 3 hours. The above method is not much different from the existing method for purifying sucralose-6-acetate by ethyl acetate recrystallization, and is mainly intended to further purify and unify the purities of sucralose-6-acetate products at different concentrations produced at different stages.

In an embodiment of the present disclosure, the purification further includes: drying a sucralose-6-acetate solid obtained by filtration with a dryer to obtain the fine sucralose-6-acetate of high purity.

Figure 2:
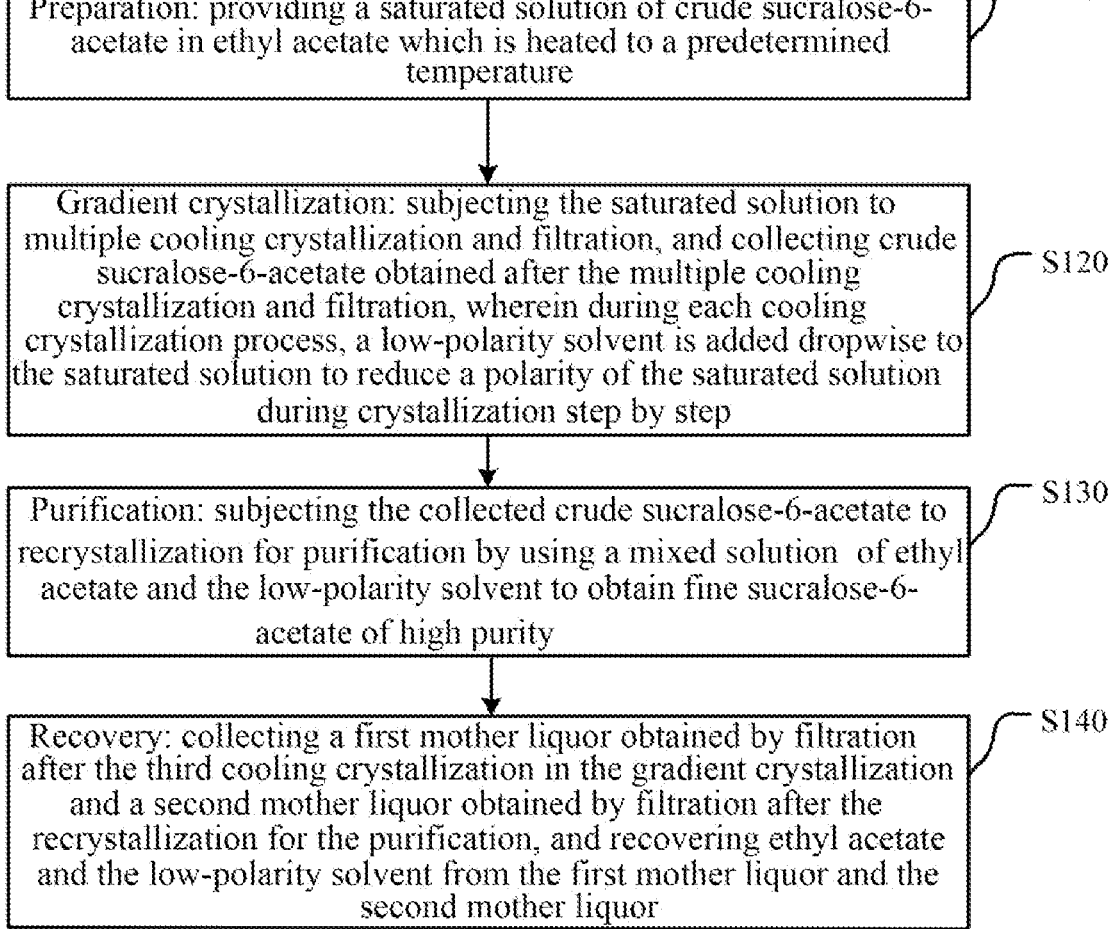
FIG. 2 is a flowchart showing the method for purifying sucralose-6-acetate according to another embodiment of the present disclosure.

FIG. 2 is a flowchart showing the method for purifying sucralose-6-acetate according to another embodiment of the present disclosure. In the embodiment of FIG. 2, the method further includes:

S140: Recovery: A first mother liquor obtained by filtration after the third cooling crystallization in the gradient crystallization and a second mother liquor obtained by filtration after the recrystallization for purification are collected, and ethyl acetate and the low-polarity solvent are recovered from the first mother liquor and the second mother liquor. Thus, in the method of the present disclosure, ethyl acetate and the low-polarity solvent could be recovered and recycled, which makes it possible to reduce the process cost.

In an embodiment of the present disclosure, in the recovery, under the condition that the low-polarity solvent includes one selected from the group consisting of n-pentane, cyclopentane, and n-hexane, the low-polarity solvent is first recovered from the first mother liquor and the second liquor, and then ethyl acetate is recovered; and under the condition that the low-polarity solvent includes one selected from the group consisting of cyclohexane, n-heptane, and cycloheptane, ethyl acetate is first recovered from the first mother liquor and the second mother liquor, and then the low-polarity solvent is recovered. When other low-polarity solvents are used, a recovery order may be adjusted according to properties such as the boiling points of the low-polarity solvents and ethyl acetate.

Figure 3:
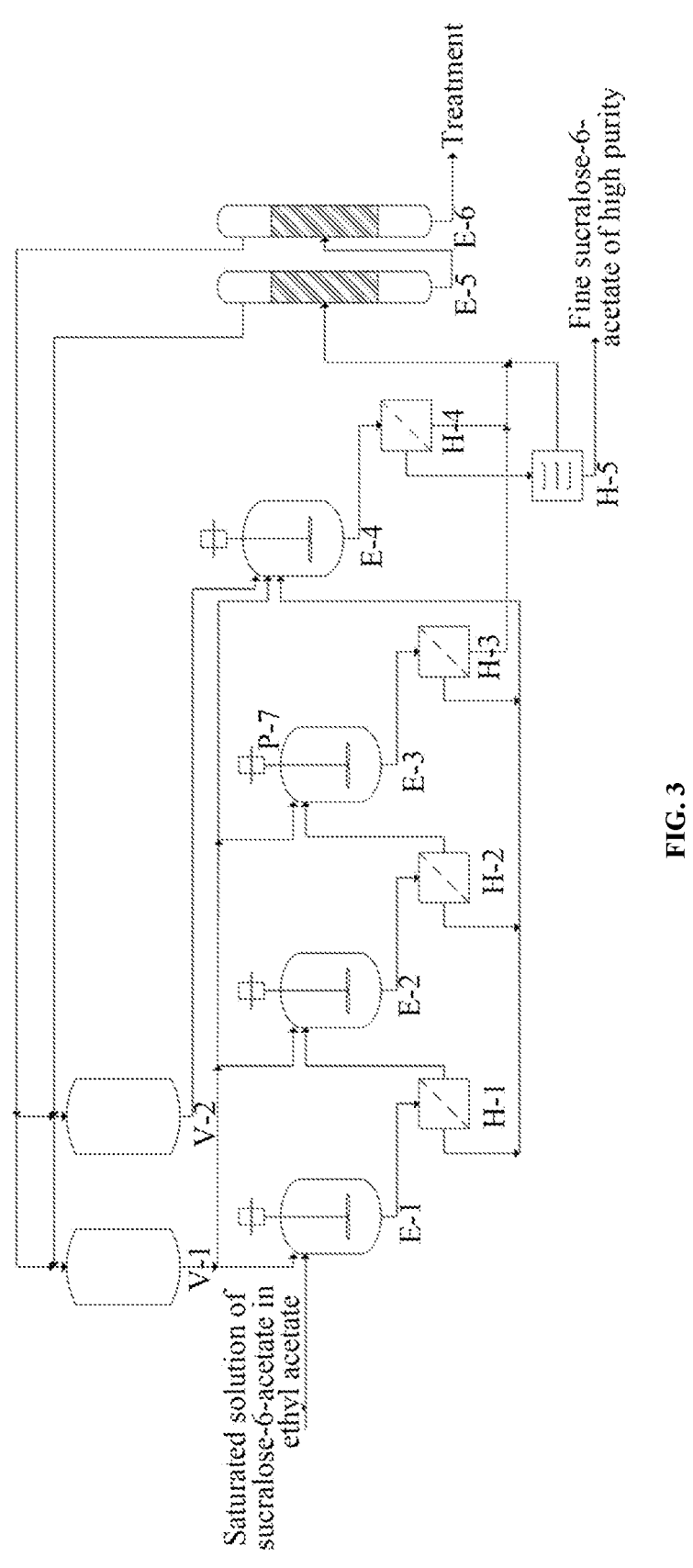
FIG. 3 is a process flowchart showing the method for purifying sucralose-6-acetate according to an embodiment of the present disclosure, where V-1 refers to a low-polarity solvent storage tank; V-2 refers to an ethyl acetate storage tank; E-1 refers to a first crystallization reactor; E-2 refers to a second crystallization reactor; E-3 refers to a third crystallization reactor; E-4 refers to a fourth crystallization reactor; E-5 and E-6 each refers to a solvent recovery tower; H-1 refers to a first solid-liquid separator; H-2 refers to a second solid-liquid separator; H-3 refers to a third solid-liquid separator; H-4 refers to a fourth solid-liquid separator; and H-5 refers to a dryer.

FIG. 3 is a process flowchart showing the method for purifying sucralose-6-acetate according to an embodiment of the present disclosure. In the process shown in FIG. 3, the purification of crude sucralose-6-acetate is achieved by conducting cooling crystallization for three times during the gradient crystallization. The following examples are illustrated with reference to the process flowchart shown in FIG. 3.

Example 1

1 m³ of a 60° C. saturated solution of crude sucralose-6-acetate in ethyl acetate (purity: greater than 99%, commercially available) (the saturated solution was prepared by dissolving crude sucralose-6-acetate obtained from a sucralose production process in ethyl acetate, and the purity was tested by high performance liquid chromatography (HPLC)) was added to a first crystallization reactor E-1, stirred at a rate of 10 r/min, and cooled to 40° C. 50 L of n-pentane (purity: greater than 99%, commercially available) was added dropwise for 5 minutes, and a resulting system was further stirred for 0.5 hours to allow a crystallization. After the crystallization was completed, a resulting mixture was subjected to a first solid-liquid separation (SLS) in a first solid-liquid separator H-1. A resulting mother liquor was transported to a second crystallization reactor E-2, cooled to 30° C., and stirred at a rate of 10 r/min. Then 100 L of n-pentane was added dropwise for 10 minutes, and a resulting system was further stirred for 0.5 hours to allow a continued crystallization. After the crystallization was completed, a resulting mixture was subjected to a second SLS in a second solid-liquid separator H-2. A resulting mother liquor was transported to a third crystallization reactor E-3, cooled to 0° C., and stirred at a rate of 30 r/min. Then 50 L of n-pentane was added dropwise for 10 minutes, and a resulting system was further stirred for 0.5 hours to allow a further crystallization. After the crystallization was completed, a resulting mixture was subjected to a third SLS in a third solid-liquid separator H-3, and a resulting mother liquor was transported to recovery towers E-5 and E-6 for solvent recovery. The gradient crystallization was completed.

2 m³ of a mixed solvent of ethyl acetate and n-pentane in a volume ratio of 1:1 was added to a fourth crystallization reactor E-4, and crude sucralose-6-acetate products obtained from the first solid-liquid separator H-1, the second solid-liquid separator H-2, and the third solid-liquid separator H-3 were added to the fourth crystallization reactor E-4. A resulting mixture was heated and stirred for complete dissolution, then cooled to −5° C., and subjected to a crystallization for 1 hour. A resulting sucralose-6-acetate solid was dried by a dryer H-5 to obtain a fine sucralose-6-acetate of high purity, and a resulting mother liquor was combined with the mother liquor obtained from the third solid-liquid separator H-3 and transported to recovery towers E-5 and E-6 for recovering ethyl acetate and the low-polarity solvent. In example 1, the low-polarity solvent was n-pentane with a lower boiling point than that of ethyl acetate. The solvent recovery tower E-5 was a low-polarity solvent recovery tower, which was configured to recover n-pentane and was connected to a low-polarity solvent storage tank V-1. The solvent recovery tower E-6 was an ethyl acetate recovery tower, which was connected to an ethyl acetate storage tank V-2. In other examples of the present disclosure, a solvent recovery order of the solvent recovery towers E-5 and E-6 was determined according to the boiling points of the low-polarity solvent and ethyl acetate, and the principle was the same, which would not be repeated. A purity of sucralose-6-acetate at each stage and a total yield of sucralose-6-acetate were shown in Table 1.

TABLE 1

| | Purity of sucralose-6-acetate at each stage and total yield of sucralose-6-acetate | | | | |
| --- | --- | --- | --- | --- | --- |
| Item | Raw material | Gradient 1 | Gradient 2 | Gradient 3 | Gradient 4 |
| Purity/% | 34.03 | 87.23 | 90.17 | 92.26 | 98.92 |
| | Total yield/% | | | | 88.24 |

Example 2

2 m³ of a 70° C. saturated solution of crude sucralose-6-acetate in ethyl acetate (purity: greater than 99%, commercially available) (the saturated solution was prepared by dissolving crude sucralose-6-acetate obtained from a sucralose production process in ethyl acetate, and the purity was tested by HPLC) was added to a first crystallization reactor E-1, stirred at a rate of 20 r/min, and cooled to 50° C. 200 L of cyclopentane was added dropwise for 20 minutes, and a resulting system was further stirred for 40 minutes to allow a crystallization. After the crystallization was completed, a resulting mixture was subjected to a first SLS in a first solid-liquid separator H-1. A resulting mother liquor was transported to a second crystallization reactor E-2, cooled to 20° C., and stirred at a rate of 15 r/min. Then 150 L of cyclopentane was added dropwise for 15 minutes, and a resulting system was further stirred for 1 hour to allow a continued crystallization. After the crystallization was completed, a resulting mixture was subjected to a second SLS in a second solid-liquid separator H-2. A resulting mother liquor was transported to a third crystallization reactor E-3, cooled to −5° C., and stirred at a rate of 15 r/min. Then 150 L of n-pentane (purity: greater than 99%, commercially available) was added dropwise for 15 minutes, and a resulting system was further stirred for 1 hour to allow a further crystallization. After the crystallization was completed, a resulting mixture was subjected to a third SLS in a third solid-liquid separator H-3, and a resulting mother liquor was transported to solvent recovery towers for solvent recovery.

2.5 m³ of a mixed solvent of ethyl acetate and n-pentane in a volume ratio of 1:0.8 was added to a fourth crystallization reactor E-4, and crude sucralose-6-acetate products obtained from the first solid-liquid separator H-1, the second solid-liquid separator H-2, and the third solid-liquid separator H-3 were added to the fourth crystallization reactor E-4. A resulting mixture was heated and stirred for complete dissolution, then cooled to −10° C., and subjected to a crystallization for 1.5 hours. A resulting sucralose-6-acetate solid was dried by a dryer H-5 to obtain a fine sucralose-6-acetate of high purity, and a resulting mother liquor was combined with the mother liquor obtained from the third solid-liquid separator H-3 and transported to solvent recovery towers for recovering ethyl acetate and the low-polarity solvent. A purity of sucralose-6-acetate at each stage and a total yield of sucralose-6-acetate were shown in Table 2.

TABLE 2

| | Purity of sucralose-6-acetate at each stage and total yield of sucralose-6-acetate | | | | |
| --- | --- | --- | --- | --- | --- |
| Item | Raw material | Gradient 1 | Gradient 2 | Gradient 3 | Gradient 4 |
| Purity/% | 36.98 | 87.69 | 90.85 | 93.57 | 97.46 |
| | Total yield/% | | | | 87.66 |

Example 3

1.5 m³ of a 65° C. saturated solution of crude sucralose-6-acetate in ethyl acetate (purity: greater than 99%, commercially available) (the saturated solution was prepared by dissolving crude sucralose-6-acetate obtained from a sucralose production process in ethyl acetate, and the purity was tested by HPLC) was added to a first crystallization reactor E-1, stirred at a rate of 15 r/min, and cooled to 45° C. 225 L of n-hexane (purity: greater than 99%, commercially available) was added dropwise for 20 minutes, and a resulting system was further stirred for 45 minutes to allow a crystallization. After the crystallization was completed, a resulting mixture was subjected to a first SLS in a first solid-liquid separator H-1. A resulting mother liquor was transported to a second crystallization reactor E-2, cooled to 25° C., and stirred at a rate of 20 r/min. Then 80 L of n-pentane was added dropwise for 10 minutes, and a resulting system was further stirred for 1 hour to allow a continued crystallization. After the crystallization was completed, a resulting mixture was subjected to a second SLS in a second solid-liquid separator H-2. A resulting mother liquor was transported to a third crystallization reactor E-3, cooled to 0° C., and stirred at a rate of 30 r/min. Then 100 L of n-pentane was added dropwise for 10 minutes, and a resulting system was further stirred for 0.5 hours to allow a further crystallization. After the crystallization was completed, a resulting mixture was subjected to a third SLS in a third solid-liquid separator H-3, and a resulting mother liquor was transported to solvent recovery towers for solvent recovery.

2 m³ of a mixed solvent of ethyl acetate and n-pentane in a volume ratio of 1:0.9 was added to a fourth crystallization reactor, and crude sucralose-6-acetate products obtained from the first solid-liquid separator H-1, the second solid-liquid separator H-2, and the third solid-liquid separator H-3 were added to the fourth crystallization reactor. A resulting mixture was heated and stirred for complete dissolution, then cooled to −8° C., and subjected to a crystallization for 1 hour. A resulting sucralose-6-acetate solid was dried by a dryer H-5 to obtain a fine sucralose-6-acetate of high purity, and a resulting mother liquor was combined with the mother liquor obtained from the third solid-liquid separator H-3 and transported to solvent recovery towers for recovering ethyl acetate and the low-polarity solvent. A purity of sucralose-6-acetate at each stage and a total yield of sucralose-6-acetate were shown in Table 3.

TABLE 3

| | Purity of sucralose-6-acetate at each stage and total yield of sucralose-6-acetate | | | | |
| --- | --- | --- | --- | --- | --- |
| Item | Raw material | Gradient 1 | Gradient 2 | Gradient 3 | Gradient 4 |
| Purity/% | 30.21 | 82.47 | 88.24 | 93.01 | 99.01 |
| | | Total yield/% | | | 88.75 |

Example 4

2 m³ of a 60° C. saturated solution of crude sucralose-6-acetate in ethyl acetate (purity: greater than 99%, commercially available) (the saturated solution was prepared by dissolving crude sucralose-6-acetate obtained from a sucralose production process in ethyl acetate, and the purity was tested by HPLC) was added to a first crystallization reactor E-1, stirred at a rate of 20 r/min, and cooled to 40° C. 280 L of cyclohexane was added dropwise for 25 minutes, and a resulting system was further stirred for 50 minutes to allow a crystallization. After the crystallization was completed, a resulting mixture was subjected to a first SLS in a first solid-liquid separator H-1. A resulting mother liquor was transported to a second crystallization reactor E-2, cooled to 30° C., and stirred at a rate of 15 r/min. Then 160 L of n-pentane (purity: greater than 99%, commercially available) was added dropwise for 15 minutes, and a resulting system was further stirred for 1 hour to allow a continued crystallization. After the crystallization was completed, a resulting mixture was subjected to a second SLS in a second solid-liquid separator H-2. A resulting mother liquor was transported to a third crystallization reactor E-3, cooled to 0° C., and stirred at a rate of 15 r/min. Then 150 L of n-pentane was added dropwise for 15 minutes, and a resulting system was further stirred for 1.5 hours to allow a further crystallization. After the crystallization was completed, a resulting mixture was subjected to a third SLS in a third solid-liquid separator H-3, and a resulting mother liquor was transported to solvent recovery towers for solvent recovery.

3 m³ of a mixed solvent of ethyl acetate and n-pentane in a volume ratio of 1:0.7 was added to a fourth crystallization reactor, and crude sucralose-6-acetate products obtained from the first solid-liquid separator H-1, the second solid-liquid separator H-2, and the third solid-liquid separator H-3 were added to the fourth crystallization reactor. A resulting mixture was heated and stirred for complete dissolution, then cooled to −10° C., and subjected to a crystallization for 2.5 hours. A resulting sucralose-6-acetate solid was dried by a dryer H-5 to obtain a fine sucralose-6-acetate of high purity, and a resulting mother liquor was combined with the mother liquor obtained from the third solid-liquid separator H-3 and transported to solvent recovery towers for recovering ethyl acetate and the low-polarity solvent. A purity of sucralose-6-acetate at each stage and a total yield of sucralose-6-acetate were shown in Table 4.

TABLE 4

| | Purity of sucralose-6-acetate at each stage and total yield of sucralose-6-acetate | | | | |
| --- | --- | --- | --- | --- | --- |
| Item | Raw material | Gradient 1 | Gradient 2 | Gradient 3 | Gradient 4 |
| Purity/% | 35.14 | 85.66 | 89.18 | 91.62 | 97.24 |
| | | Total yield/% | | | 88.25 |

Example 5

1 m³ of a 70° C. saturated solution of crude sucralose-6-acetate in ethyl acetate (purity: greater than 99%, commercially available) (the saturated solution was prepared by dissolving crude sucralose-6-acetate obtained from a sucralose production process in ethyl acetate, and the purity was tested by HPLC) was added to a first crystallization reactor E-1, stirred at a rate of 10 r/min, and cooled to 40° C. 70 L of n-heptane (purity: greater than 99%, commercially available) was added dropwise for 5 minutes, and a resulting system was further stirred for 0.5 hours to allow a crystallization. After the crystallization was completed, a resulting mixture was subjected to a first SLS in a first solid-liquid separator H-1. A resulting mother liquor was transported to a second crystallization reactor E-2, cooled to 20° C., and stirred at a rate of 10 r/min. Then 100 L of n-pentane was added dropwise for 10 minutes, and a resulting system was further stirred for 0.5 hours to allow a continued crystallization. After the crystallization was completed, a resulting mixture was subjected to a second SLS in a second solid-liquid separator H-2. A resulting mother liquor was transported to a third crystallization reactor E-3, cooled to −6° C., and stirred at a rate of 10 r/min. Then 50 L of n-pentane was added dropwise for 10 minutes, and a resulting system was further stirred for 0.5 hours to allow a further crystallization. After the crystallization was completed, a resulting mixture was subjected to a third SLS in a third solid-liquid separator H-3, and a resulting mother liquor was transported to solvent recovery towers for solvent recovery.

1.5 m³ of a mixed solvent of ethyl acetate and n-pentane in a volume ratio of 1:1 was added to a fourth crystallization reactor, and crude sucralose-6-acetate products obtained from the first solid-liquid separator H-1, the second solid-liquid separator H-2, and the third solid-liquid separator H-3 were added to the fourth crystallization reactor. A resulting mixture was heated and stirred for complete dissolution, then cooled to –10° C., and subjected to a crystallization for 0.5 hours. A resulting sucralose-6-acetate solid was dried by a dryer H-5 to obtain a fine sucralose-6-acetate of high purity, and a resulting mother liquor was combined with the mother liquor obtained from the third solid-liquid separator H-3 and transported to solvent recovery towers for recovering ethyl acetate and the low-polarity solvent. A purity of sucralose-6-acetate at each stage and a total yield of sucralose-6-acetate were shown in Table 5.

Example 6

3 m³ of a 60° C. saturated solution of crude sucralose-6-acetate in ethyl acetate (purity: greater than 99%, commercially available) (the saturated solution was prepared by dissolving crude sucralose-6-acetate obtained from a sucralose production process in ethyl acetate, and the purity was tested by HPLC) was added to a first crystallization reactor E-1, stirred at a rate of 30 r/min, and cooled to 45° C. 240 L of cycloheptane (purity: greater than 99%, commercially available) was added dropwise for 25 minutes, and a resulting system was further stirred for 1 hour to allow a crystallization. After the crystallization was completed, a resulting mixture was subjected to a first SLS in a first solid-liquid separator H-1. A resulting mother liquor was transported to a second crystallization reactor E-2, cooled to 20° C., and stirred at a rate of 15 r/min. Then 180 L of n-pentane was added dropwise for 15 minutes, and a resulting system was further stirred for 1.5 hours to allow a continued crystallization. After the crystallization was completed, a resulting mixture was subjected to a second SLS in a second solid-liquid separator H-2. A resulting mother liquor was transported to a third crystallization reactor E-3, cooled to –3° C., and stirred at a rate of 15 r/min. Then 200 L of n-pentane was added dropwise for 20 minutes, and a resulting system was further stirred for 2 hours to allow a further crystallization. After the crystallization was completed, a resulting mixture was subjected to a third SLS in a third solid-liquid separator H-3, and a resulting mother liquor was transported to solvent recovery towers for solvent recovery.

4.5 m³ of a mixed solvent of ethyl acetate and n-pentane in a volume ratio of 1:0.5 was added to a fourth crystallization reactor, and crude sucralose-6-acetate products obtained from the first solid-liquid separator H-1, the second solid-liquid separator H-2, and the third solid-liquid separator H-3 were added to the fourth crystallization reactor. A resulting mixture was heated and stirred for complete dissolution, then cooled to –8° C., and subjected to a crystallization for 3 hours. A resulting sucralose-6-acetate solid was dried by a dryer H-5 to obtain a fine sucralose-6-acetate of high purity, and a resulting mother liquor was combined with the mother liquor obtained from the third solid-liquid separator H-3 and transported to solvent recovery towers for recovering ethyl acetate and the low-polarity solvent. A purity of sucralose-6-acetate at each stage and a total yield of sucralose-6-acetate were shown in Table 6.

TABLE 6

| | Purity of sucralose-6-acetate at each stage and total yield of sucralose-6-acetate | | | | |
|---|---|---|---|---|---|
| Item | Raw material | Gradient 1 | Gradient 2 | Gradient 3 | Gradient 4 |
| Purity/% | 36.55 | 89.52 | 93.11 | 96.00 | 98.43 |
| | Total yield/% | | | | 89.27 |

Example 7

4 m³ of a 70° C. saturated solution of crude sucralose-6-acetate in ethyl acetate (purity: greater than 99%, commercially available) (the saturated solution was prepared by dissolving crude sucralose-6-acetate obtained from a sucralose production process in ethyl acetate, and the purity was tested by HPLC) was added to a first crystallization reactor E-1, stirred at a rate of 30 r/min, and cooled to 50° C. 360 L of cyclohexane (purity: greater than 99%, commercially available) was added dropwise for 30 minutes, and a resulting system was further stirred for 1 hour to allow a crystallization. After the crystallization was completed, a resulting mixture was subjected to a first SLS in a first solid-liquid separator H-1. A resulting mother liquor was transported to a second crystallization reactor E-2, cooled to 30° C., and stirred at a rate of 20 r/min. Then 200 L of n-pentane was added dropwise for 20 minutes, and a resulting system was further stirred for 1.5 hours to allow a continued crystallization. After the crystallization was completed, a resulting mixture was subjected to a second SLS in a second solid-liquid separator H-2. A resulting mother liquor was transported to a third crystallization reactor E-3, cooled to –1° C., and stirred at a rate of 10 r/min. Then 400 L of n-pentane was added dropwise for 30 minutes, and a resulting system was further stirred for 2 hours to allow a further crystallization. After the crystallization was completed, a resulting mixture was subjected to a third SLS in a third solid-liquid separator H-3, and a resulting mother liquor was transported to solvent recovery towers for solvent recovery.

5 m³ of a mixed solvent of ethyl acetate and n-pentane in a volume ratio of 1:0.6 was added to a fourth crystallization reactor, and crude sucralose-6-acetate products obtained from the first solid-liquid separator H-1, the second solid-liquid separator H-2, and the third solid-liquid separator H-3 were added to the fourth crystallization reactor. A resulting mixture was heated and stirred for complete dissolution, then cooled to –9° C., and subjected to a crystallization for 3 hours. A resulting sucralose-6-acetate solid was dried by a dryer H-5 to obtain a fine sucralose-6-acetate of high purity, and a resulting mother liquor was combined with the mother liquor obtained from the third solid-liquid separator H-3 and transported to solvent recovery towers for recovering ethyl acetate and the low-polarity solvent. A purity of sucralose-6-acetate at each stage and a total yield of sucralose-6-acetate were shown in Table 7.

TABLE 7

| | Purity of sucralose-6-acetate at each stage and total yield of sucralose-6-acetate | | | | |
|---|---|---|---|---|---|
| Item | Raw material | Gradient 1 | Gradient 2 | Gradient 3 | Gradient 4 |
| Purity/% | 36.89 | 88.16 | 91.25 | 95.56 | 98.58 |
| | Total yield/% | | | | 86.13 |

Example 8

3.5 m³ of a 65° C. saturated solution of crude sucralose-6-acetate in ethyl acetate (purity: greater than 99%, commercially available) (the saturated solution was prepared by dissolving crude sucralose-6-acetate obtained from a sucralose production process in ethyl acetate, and the purity was tested by HPLC) was added to a first crystallization reactor E-1, stirred at a rate of 25 r/min, and cooled to 40° C. 420

L of n-heptane (purity: greater than 99%, commercially available) was added dropwise for 30 minutes, and a resulting system was further stirred for 1 hour to allow a crystallization. After the crystallization was completed, a resulting mixture was subjected to a first SLS in a first solid-liquid separator H-1. A resulting mother liquor was transported to a second crystallization reactor E-2, cooled to 20° C., and stirred at a rate of 30 r/min. Then 350 L of n-pentane was added dropwise for 30 minutes, and a resulting system was further stirred for 1.5 hours to allow a continued crystallization. After the crystallization was completed, a resulting mixture was subjected to a second SLS in a second solid-liquid separator H-2. A resulting mother liquor was transported to a third crystallization reactor E-3, cooled to −4° C., and stirred at a rate of 10 r/min. Then 175 L of n-pentane was added dropwise for 15 minutes, and a resulting system was further stirred for 2 hours to allow a further crystallization. After the crystallization was completed, a resulting mixture was subjected to a third SLS in a third solid-liquid separator H-3, and a resulting mother liquor was transported to solvent recovery towers for solvent recovery.

4 m³ of a mixed solvent of ethyl acetate and n-pentane in a volume ratio of 1:0.5 was added to a fourth crystallization reactor, and crude sucralose-6-acetate products obtained from the first solid-liquid separator H-1, the second solid-liquid separator H-2, and the third solid-liquid separator H-3 were added to the fourth crystallization reactor. A resulting mixture was heated and stirred for complete dissolution, then cooled to −10° C., and subjected to a crystallization for 2.5 hours. A resulting sucralose-6-acetate solid was dried by a dryer H-5 to obtain a fine sucralose-6-acetate of high purity, and a resulting mother liquor was combined with the mother liquor obtained from the third solid-liquid separator H-3 and transported to solvent recovery towers for recovering ethyl acetate and the low-polarity solvent. A purity of sucralose-6-acetate at each stage and a total yield of sucralose-6-acetate were shown in Table 8.

TABLE 8

| | Purity of sucralose-6-acetate at each stage and total yield of sucralose-6-acetate | | | | |
| --- | --- | --- | --- | --- | --- |
| Item | Raw material | Gradient 1 | Gradient 2 | Gradient 3 | Gradient 4 |
| Purity/% | 32.71 | 85.23 | 90.99 | 93.77 | 99.05 |
| Total yield/% | | | | | 87.65 |

Example 9

2.5 m³ of a 70° C. saturated solution of crude sucralose-6-acetate in ethyl acetate (purity: greater than 99%, commercially available) (the saturated solution was prepared by dissolving crude sucralose-6-acetate obtained from a sucralose production process in ethyl acetate, and the purity was tested by HPLC) was added to a first crystallization reactor E-1, stirred at a rate of 15 r/min, and cooled to 50° C. 175 L of cyclopentane (purity: greater than 99%, commercially available) was added dropwise for 15 minutes, and a resulting system was further stirred for 55 minutes to allow a crystallization. After the crystallization was completed, a resulting mixture was subjected to a first SLS in a first solid-liquid separator H-1. A resulting mother liquor was transported to a second crystallization reactor E-2, cooled to 25° C., and stirred at a rate of 15 r/min. Then 200 L of n-pentane was added dropwise for 20 minutes, and a resulting system was further stirred for 1.5 hours to allow a continued crystallization. After the crystallization was completed, a resulting mixture was subjected to a second SLS in a second solid-liquid separator H-2. A resulting mother liquor was transported to a third crystallization reactor E-3, cooled to −1° C., and stirred at a rate of 10 r/min. Then 125 L of n-pentane was added dropwise for 10 minutes, and a resulting system was further stirred for 1.5 hours to allow a further crystallization. After the crystallization was completed, a resulting mixture was subjected to a third SLS in a third solid-liquid separator H-3, and a resulting mother liquor was transported to solvent recovery towers for solvent recovery.

3.5 m³ of a mixed solvent of ethyl acetate and n-pentane in a volume ratio of 1:0.7 was added to a fourth crystallization reactor, and crude sucralose-6-acetate products obtained from the first solid-liquid separator H-1, the second solid-liquid separator H-2, and the third solid-liquid separator H-3 were added to the fourth crystallization reactor. A resulting mixture was heated and stirred for complete dissolution, then cooled to −7° C., and subjected to a crystallization for 2 hours. A resulting sucralose-6-acetate solid was dried by a dryer H-5 to obtain a fine sucralose-6-acetate of high purity, and a resulting mother liquor was combined with the mother liquor obtained from the third solid-liquid separator H-3 and transported to solvent recovery towers for recovering ethyl acetate and the low-polarity solvent. A purity of sucralose-6-acetate at each stage and a total yield of sucralose-6-acetate were shown in Table 9.

TABLE 9

| | Purity of sucralose-6-acetate at each stage and total yield of sucralose-6-acetate | | | | |
| --- | --- | --- | --- | --- | --- |
| Item | Raw material | Gradient 1 | Gradient 2 | Gradient 3 | Gradient 4 |
| Purity/% | 37.34 | 87.68 | 91.39 | 94.17 | 98.81 |
| Total yield/% | | | | | 89.73 |

In summary, in the method for purifying sucralose-6-acetate of the present disclosure, ethyl acetate is used as an initial solvent for cooling crystallization of sucralose-6-acetate, and a low-polarity solvent is added step by step with the decrease of temperature to make the polarity of the mixed solvent show a trend of gradient reduction during the crystallization, such that impurities could be effectively separated at different gradient stages, which enables high single-pass crystallization yield and efficiency, ensures the purity of a crystallization product, and reduces the number of crystallization times and the consumption of the organic solvent, thereby leading to high product yield, purity, and quality.

The above are merely specific examples of the present disclosure, and under the above instruction of the present disclosure, those skilled in the art may make other improvements or variations on the basis of the above examples. Those skilled in the art should understand that the above specific description is merely intended to well explain the present disclosure, and a protection scope of the present disclosure shall be defined by the protection scope of the claims.

What is claimed is:

1. A method for purifying sucralose-6-acetate, comprising:

preparation: providing a saturated solution of crude sucralose-6-acetate in ethyl acetate which is heated to a predetermined temperature;

gradient crystallization: subjecting the saturated solution to multiple cooling crystallization and filtration, and collecting crude sucralose-6-acetate obtained after the multiple cooling crystallization and filtration, wherein during each cooling crystallization process, a low-polarity solvent is added dropwise to the saturated solution to reduce a polarity of the saturated solution during crystallization step by step; and purification: subjecting a resulting collected crude sucralose-6-acetate to recrystallization for purification by using a mixed solution of ethyl acetate and the low-polarity solvent to obtain a purified sucralose-6-acetate;

wherein in the gradient crystallization, the saturated solution is subjected to the multiple cooling crystallization three times, wherein the multiple cooling crystallization comprises a first cooling crystallization, a second cooling crystallization, and a third cooling crystallization, wherein the first cooling crystallization is conducted at a temperature of 40° C. to 50° C., the second cooling crystallization is conducted at a temperature of 20° C. to 30° C., and the third cooling crystallization is conducted at a temperature of −10° C. to 0° C.

2. The method for purifying sucralose-6-acetate of claim 1, wherein the predetermined temperature of the saturated solution of crude sucralose-6-acetate in ethyl acetate is in a range of 60° C. to 70° C.

3. The method for purifying sucralose-6-acetate of claim 1, wherein the low-polarity solvent is one or more selected from the group consisting of n-pentane, cyclopentane, n-hexane, cyclohexane, n-heptane, and cycloheptane.

4. The method for purifying sucralose-6-acetate of claim 1, wherein in the gradient crystallization, the low-polarity solvent is added dropwise for 5 minutes to 30 minutes in an amount of 5% to 15% of a volume of the saturated solution during each cooling crystallization process;

the first cooling crystallization is conducted for 0.5 hours to 1 hour, the second cooling crystallization is conducted for 0.5 hours to 1.5 hours, and the third cooling crystallization is conducted for 0.5 hours to 2 hours; and during each cooling crystallization process, a resulting solution is stirred at a rate of 10 r/min to 30 r/min.

5. The method for purifying sucralose-6-acetate of claim 1, wherein in the purification, the crude sucralose-6-acetate is dissolved at a temperature of 50° C. to 70° C. for recrystallization; the mixed solution of ethyl acetate and the low-polarity solvent is stirred at a rate of 60 r/min to 100 r/min; a volume ratio of ethyl acetate to the low-polarity solvent is in a range of 1: (0.5-1); and the recrystallization is conducted at a temperature of −10° C. to 0° C. for 0.5 hours to 3 hours.

6. The method for purifying sucralose-6-acetate of claim 1, wherein the purification further comprises: drying a sucralose-6-acetate solid obtained by filtration with a dryer to obtain the purified sucralose-6-acetate.

7. The method for purifying sucralose-6-acetate of claim 1, further comprising:

recovery: collecting a first mother liquor obtained by filtration after the third cooling crystallization in the gradient crystallization and a second mother liquor obtained by filtration after the recrystallization for the purification, and recovering ethyl acetate and the low-polarity solvent from the first mother liquor and the second mother liquor.

8. The method for purifying sucralose-6-acetate of claim 7, wherein in the recovery, under the condition that the low-polarity solvent comprises one selected from the group consisting of n-pentane, cyclopentane, and n-hexane, the low-polarity solvent is first recovered from the first mother liquor and the second mother liquor, and then ethyl acetate is recovered; and under the condition that the low-polarity solvent comprises one selected from the group consisting of cyclohexane, n-heptane, and cycloheptane, and ethyl acetate is first recovered from the first mother liquor and the second mother liquor, and then the low-polarity solvent is recovered.

* * * * *